(12) United States Patent
Shchervinsky

(10) Patent No.: US 6,173,206 B1
(45) Date of Patent: Jan. 9, 2001

(54) TEMPORARY PACING WIRE ANCHOR

(75) Inventor: Semyon Shchervinsky, Whitehouse Station, NJ (US)

(73) Assignee: Ethicon, Inc., Somerville, NJ (US)

( * ) Notice: Under 35 U.S.C. 154(b), the term of this patent shall be extended for 0 days.

(21) Appl. No.: 09/307,537

(22) Filed: May 7, 1999

(51) Int. Cl.⁷ ...................................................... A61N 1/05
(52) U.S. Cl. .............................................................. 607/132
(58) Field of Search ............................................. 607/132

(56) References Cited

U.S. PATENT DOCUMENTS

| | | | |
|---|---|---|---|
| 3,902,501 | 9/1975 | Citron et al. ........................ | 128/418 |
| 4,444,207 | 4/1984 | Robicsek .............................. | 128/785 |
| 4,628,944 | 12/1986 | MacGregor et al. ................. | 128/785 |
| 4,633,880 | 1/1987 | Osypka et al. ....................... | 128/642 |
| 5,314,463 | 5/1994 | Camps et al. ........................ | 607/129 |

*Primary Examiner*—William E. Kamm

(57) ABSTRACT

A temporary cardiac pacing wire (TPW) includes an electrically conductive flexible wire having a bioabsorbable anchor near its distal end. The anchor includes a tubular section that surrounds the wire and a leg that extends from the tubular section at an acute angle to the wire. The bioabsorbable anchor causes minimal trauma to the heart when it is inserted with the TPW, but securely anchors the TPW in the heart. After the TPW is no longer needed, it can be removed, again with minimal trauma to the heart, leaving behind only the bioabsorbable anchor. The bioabsorbable anchor is suitable for use with both monopolar and bipolar TPWs.

8 Claims, 4 Drawing Sheets

TEMPORARY PACING WIRE ANCHOR

BACKGROUND OF THE INVENTION

1. Field of the Invention

This invention relates to a surgical electrode and, more particularly, to a temporary cardiac pacing wire having a bioabsorbable anchor for anchoring the wire in a heart.

2. Description of the Related Art

Devices to stimulate or regulate cardiac function have been known and used for decades. They involve a power source (pacemaker) and a surgical electrode to attach the source to the heart. They are generally of two types.

Implantable pacers are intended for long-term use and, as the name suggests, are entirely implanted in the body. The other type is intended for temporary use. The pacemaker is located outside the body and is connected to the heart by a surgical electrode called a "temporary pacing wire." Although surgical electrodes are used for preparing electrocardiograms and other applications, for the sake of brevity, the description that follows is focused on temporary pacing wires. In general, such connectors are constructed of a number of fine, stainless steel wires twisted together to form a single, flexible, multi-strand electrode wire. The major portion of the wire is insulated with a polyethylene, polytetrafluoroethylene, silicone, nylon, or other nonconducting coating, with a short length of wire at either end left uninsulated. To the distal uninsulated end of the electrode wire there is attached, by swaging or other means, a fine curved needle for piercing the heart tissue to place the uninsulated end of the electrode in the myocardium. At the proximal end of the electrode wire is affixed a straight (e.g., Keith-type) cutting needle for piercing the thoracic wall to lead the electrode to an outer point for connection with the pacemaker. Once that has been accomplished, the needle, or the sharp, pointed end of it, is clipped off and the electrode is ready to be attached to the pacemaker as required to stimulate or regulate the beating of the heart. A single setup involves two electrodes; i.e., two temporary pacing wires.

During the time that the temporary pacing wire is performing its function, a distal end of the electrode wire must be anchored in the heart. The anchor must be secure, lest the continually beating heart cause the wire to be expelled from the heart. When the need for the pacing wire has passed, it is necessary to remove from the body the wire that runs from the external pacemaker to the electrode in the heart. Thus, the requirements for a temporary pacing wire are to some extent in conflict. It must securely attach the electrode wire to the heart during an initial period, then be easily removed from the heart without reopening the surgical site.

U.S. Pat. No. 3,902,501, issued on Sep. 2, 1975 to Citron et al., discloses an endocardial electrode that has a plurality of tines that extend from the electrode adjacent to the tip and form an acute angle with the electrode body. The tines are preferably restrained during insertion of the device.

U.S. Pat. No. 4,444,207, issued on Apr. 24, 1984 to Robicsek, discloses a method of anchoring a temporary pacing wire that has a wire conductor with a curved needle at its distal end. The method involves passing the curved needle through the wall of the heart and then through a disk-shaped button. The button is moved into contact with the heart and, after the distal end of the wire is severed, the button serves to retain the wire in a fixed position relative to the heart wall.

U.S. Pat. No. 4,628,444, issued on Dec. 16, 1986 to MacGregor et al., discloses a permanent cardiac pacing lead that has an electrode with a plurality of biodegradable fins adjacent to its tip. The electrode becomes permanently fixed in the heart over a period of weeks, during which time the fins are gradually absorbed.

U.S. Pat. No. 5,314,463, issued on May 24, 1994 to Camps et al., discloses a bipolar temporary pacing wire whose distal end has a fixation coil that is embedded in the heart wall for retaining the device in the heart.

None of the prior art pacing wire devices combine a bioabsorbable anchor with the means to remove the other elements of the device with minimal heart trauma.

SUMMARY OF THE INVENTION

In accordance with the present invention,
a temporary cardiac pacing wire (TPW) comprises
   (a) a filament, electrically conductive over at least a part of its length, having a proximal end and a distal end,
   (b) a curved needle attached to the distal end of the filament, and
   (c) a bioabsorbable anchor attached to the filament near the distal end, the anchor comprising
      (i) a tubular section surrounding the filament and
      (ii) a leg extending from the tubular section
at an acute angle to the filament.

The TPW of this invention has a bioabsorbable anchor that is not removed from the heart. Thus, removing the rest of the TPW requires only disengaging it from the anchor and pulling it out of the body. That removal method causes only minimal trauma to the heart, compared with the trauma that is caused by prior art devices that require an anchor to be removed through heart muscle.

Note that in this specification and the appended claims we use the terms "filament" and "wire" interchangeably. Within the constraints described below, the filament/wire of the temporary pacing wire may, over part of its length, be conductive or non-conductive, flexible or rigid, and single- or multi-strand.

DETAILED DESCRIPTION OF THE INVENTION

This invention relates to an anchor for a temporary pacing wire (TPW) that provides secure attachment of the TPW to the heart, while permitting the connection from outside the body to be removed with minimal trauma. The anchor itself is bioabsorbable and does not, therefore, need to be removed from the body.

Figure 1:
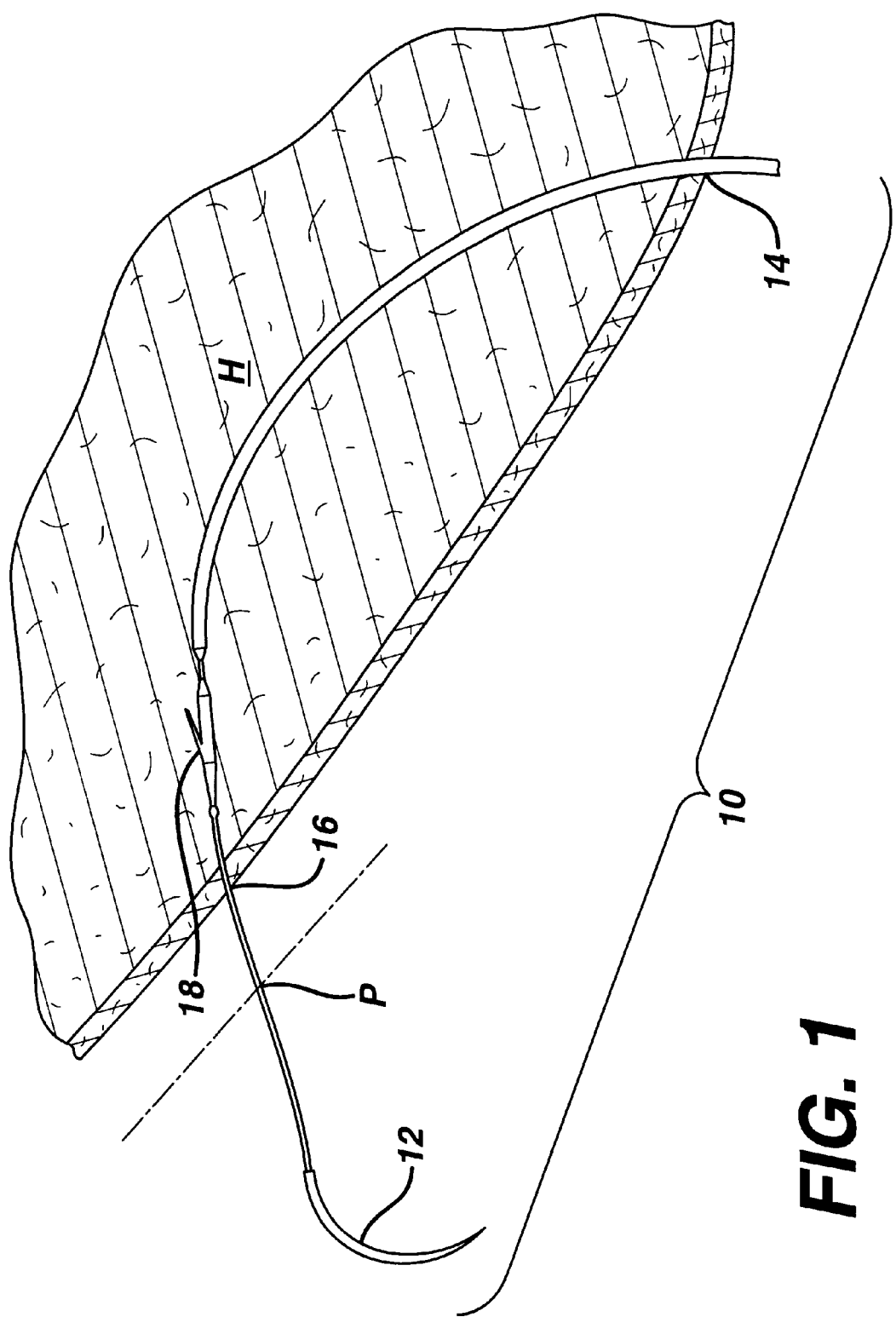
FIG. 1 is a schematic of a distal section of a temporary pacing wire and its position relative to a heart wall.

FIG. 1 depicts a distal section 10 of a TPW and a cross section of part of a heart H. Note that the proximal end of the TPW (not shown) is connected to a source of electrical pulses, located outside the body, and the electrically conductive part of the TPW extends from outside the body to the section shown. As shown, the TPW has been put in place by curved needle 12 having first been inserted into the heart at a first location 14 and having then emerged from the heart at a second location 16. The anchor 18 preferably remains in the myocardium of the heart, as shown, but alternatively may be pulled through the myocardium and be outside the heart. After the TPW and anchor are in place, the TPW is cut between the anchor and curved needle (at P) and the needle is discarded.

Figure 2:
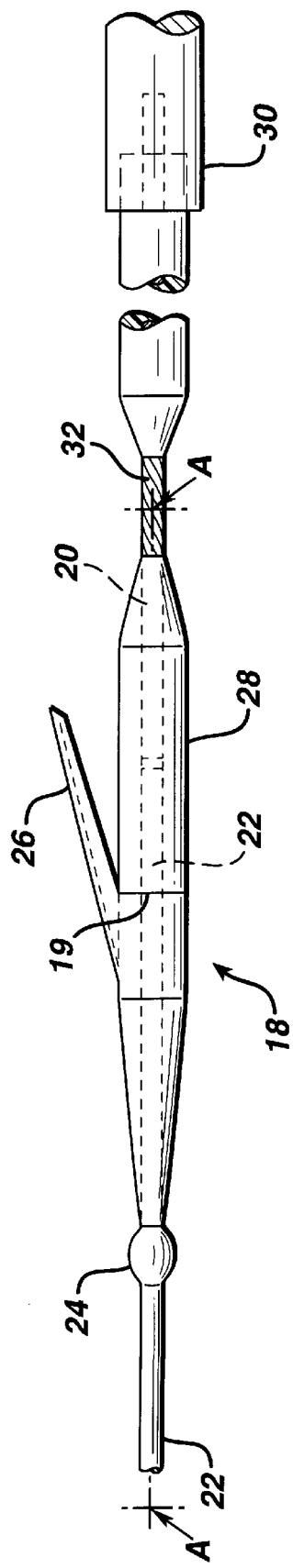
FIG. 2 is a side view of an anchor of this invention and adjoining elements of a temporary pacing wire.
Figure 3:
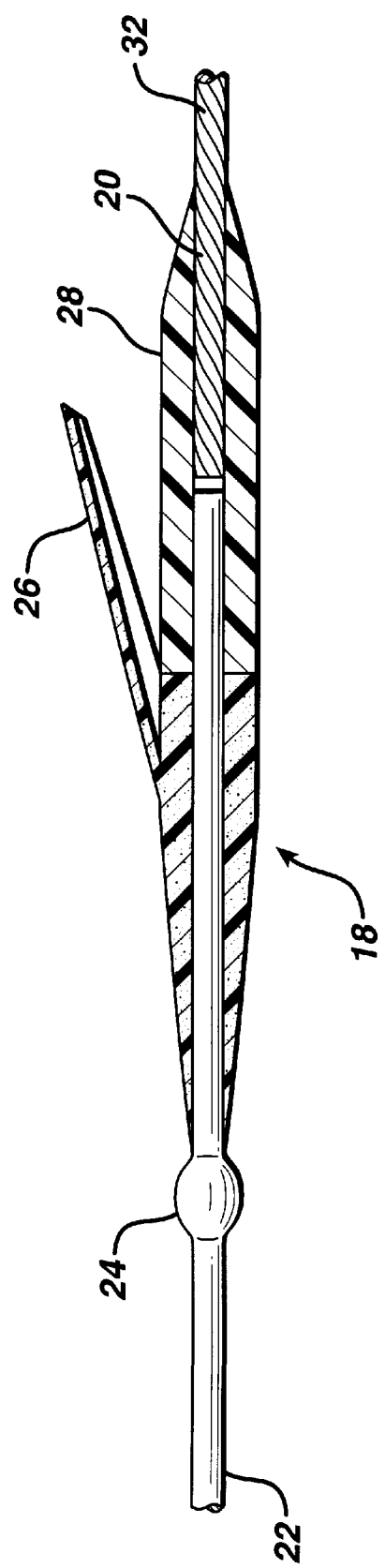
FIG. 3 is a cross section of the device of FIG. 2.

FIG. 2 shows the anchor 18 and the adjoining elements in more detail, and FIG. 3 is a section through line A—A of FIG. 2. In the embodiment depicted there, the conductive part 20 of the TPW extends substantially to the proximal end 19 of anchor 18. The distal (left) end of the TPW, to which the curved needle is initially attached, comprises suture material 22. This embodiment is generally preferred over the embodiment where the entire length of the TPW is conductive for several reasons. Suture material is more flexible, making the insertion process easier. In addition, the electrical pacing signal is weaker when the electrode protrudes from the heart. Finally, if the conductive wire 20 protrudes from the heart, it can inadvertently contact other tissue, which is undesirable. Anchor 18 surrounds, but is not joined to, suture 22. Consequently, suture 22 preferably has an enlarged section 24 that prevents the suture from being inadvertently pulled out of anchor 18 by the beating of the heart. Leg 26 preferably protrudes from the proximal part of anchor 18 at an acute angle to perform the anchoring function. During insertion of the device into the heart, anchor 18 causes minimal resistance and minimal trauma. Tubular stop 28 is joined to suture 22 and conductive wire 20 and prevents anchor 18 from sliding to the right during insertion. At the proximal end of the TPW, after the cutting needle has pierced the thoracic wall to lead the electrode outside the body, the needle is clipped or broken off, and the proximal end 30 of the TPW can be attached to an external source of electrical pulses. Preferably, conductive wire 20 is stranded metal for greater flexibility. If stop 28 is an insulator, bare wire section 32 of conductive wire 20 serves as an electrode. If stop 28 is conducting, it is in electrical contact with conductive wire 20, insulation 34 can extend to the stop, and no bare section is needed.

The embodiment depicted in FIGS. 1–3 is monopolar, providing a single electrode, and necessitates a second, similar device being implanted into the heart a short distance away to provide a second electrode.

Figure 4:
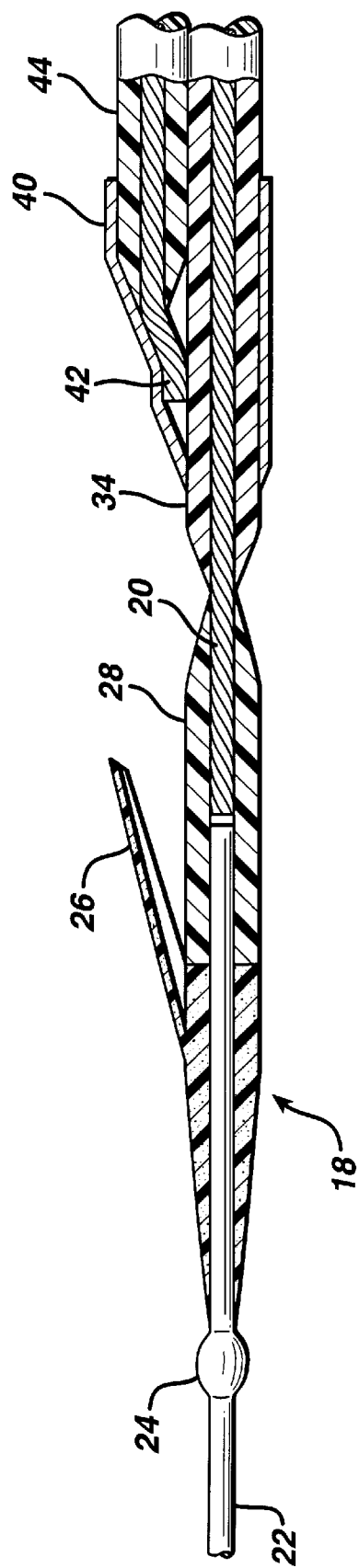
FIG. 4 is a cross section of the distal end of a bipolar temporary pacing wire.

FIG. 4 depicts a bipolar device, which is a preferred embodiment of the present device. In this embodiment, a second electrode 40 is included. In the particular embodiment shown, the electrode is a conductive bushing that surrounds the distal ends of insulation 34 and 44 and is in electrical contact with a second conductive wire 42. Alternatively, bare wire 42 could alone form the electrode. The other (right) end of conductive wire 42 (not shown) is connected to the external source of electrical pulses referred to above. When the bipolar device of FIG. 4 is implanted, no second device is needed. Consequently, no second puncture of the heart wall is needed and the TPW insertion process is correspondingly simpler. Additional details of the bipolar TPW appear in U.S. Pat. No. 4,633,880, issued on Jan. 6, 1987 to Osypka et al., incorporated herein by reference.

When the TPW is no longer needed, a force (to the right) is exerted from outside the body to withdraw it. Tubular stop 28 transmits that force to suture 22 (in the embodiment in which conductive wire 20 does not extend to the distal end of the device), and the suture is withdrawn through anchor 18. The withdrawal force must overcome the resistance caused by enlarged section 24 of the suture. When conductive wire 20 extends to the distal end of the TPW (no suture used), then it is preferably stranded, so that enlarged section 24 is readily deformed for removing the TPW. In either case, the enlarged section is typically sized to provide a resistive force of about 100 g, or less, well below the force of at least about 250 g, or more, that anchor 18 can withstand, without being displaced. Thus, after the TPW is no longer needed, the rest of it is removed and only the bioabsorbable anchor 18 remains in the body.

TPW anchor 18 can be fabricated (preferably, molded as a single piece) from any suitable bioabsorbable material(s). Preferred materials are polymers prepared from the following monomers: glycolide, L-lactide, Dlactide, meso-lactide, 1,4-dioxan-2-one, trimethylene carbonate, and e-caprolactone. These monomers can be used to prepare homopolymers, as well as copolymers, in various combinations. Preferred materials are the segmented glycolide/e-caprolactone copolymers that are used to make polyglecaprone (MONOCRYL*) sutures, the random glycolide lactide copolymers that are used to make polyglactin (VICRYL*) sutures, and the homopolymer polydioxanone, which is used to make PDS*II sutures. Information concerning these materials and processes appears in U.S. Pat. Nos. 4,490,326; 4,878,890; 5,468,253; and 5,713,920.

We claim:

1. A temporary cardiac pacing wire (TPW) comprising
   (a) a filament, electrically conductive over at least a part of its length, having a proximal end and a distal end,
   (b) a curved needle attached to the distal end of the filament, and
   (c) a bioabsorbable anchor attached to the filament near the distal end, the anchor comprising
      (i) a tubular section surrounding the filament and
      (ii) a leg extending from the tubular section at an acute angle to the filament.

2. The TPW of claim 1 in which the electrically conductive part of the TPW extends from the proximal end of the TPW substantially to the proximal end of the anchor.

3. The TPW of claim 2 further comprising a conductive member surrounding, and in electrical contact with, a section of the electrically conductive part of the TPW that adjoins the proximal end of the anchor.

4. The TPW of claim 1 in which the distal end of the TPW comprises a suture material.

5. The TPW of claim 1 in which the tubular section has a substantially cylindrical central opening having a diameter that is smaller than the diameter of a section of the TPW between the distal end and the anchor.

6. The TPW of claim 1 in which the electrically conductive part of the TPW comprises stranded metal.

7. The TPW of claim 1 further comprising a second filament, electrically conductive over substantially its entire length, and having an uninsulated distal end.

8. A temporary cardiac pacing wire (TPW) comprising
   (a) a filament, electrically conductive over at least a part of its length, having a proximal end and a distal end,
   (b) a curved needle attached to the distal end of the filament, and
   (c) an anchor attached to the filament near the distal end, the anchor comprising
      (i) a tubular section surrounding the filament and
      (ii) a leg extending from the tubular section at an acute angle to the filament.

* * * * *